United States Patent [19]

Kalogris

[11] 4,140,766

[45] Feb. 20, 1979

[54] METHOD AND COMPOSITION FOR THERAPY AND CONTROL OF BOVINE MASTITIS

[76] Inventor: Theodore P. Kalogris, 6115 Rannoch Rd., Bethesda, Md. 20034

[21] Appl. No.: 844,195

[22] Filed: Oct. 25, 1977

[51] Int. Cl.$^2$ .................. A61K 33/18; A61K 31/19
[52] U.S. Cl. .................................. 424/150; 424/317
[58] Field of Search .............................. 424/150, 317

[56] References Cited

U.S. PATENT DOCUMENTS

| | | | |
|---|---|---|---|
| 3,308,014 | 3/1967 | Cantor et al. | 424/150 |
| 4,012,504 | 3/1977 | Echols | 424/150 |

OTHER PUBLICATIONS

Klussendorf–The North American Veterinarian, May, 1942, pp. 314 & 315.
U.S. Dispensatory–25th Edition (1955), p. 9.

Primary Examiner—Sam Rosen
Attorney, Agent, or Firm—Dennison, Dennison, Meserole & Pollack

[57] ABSTRACT

A method is disclosed for the therapy and control of subclinical and clinical mastitis by the oral or parenteral administration of a composition having as active constituents iodine, potassium iodide and an aqueous solution of acetic acid made from the alcoholic and subsequent acetous fermentations of the juice of apples, in an aqueous carrier.

8 Claims, No Drawings

METHOD AND COMPOSITION FOR THERAPY AND CONTROL OF BOVINE MASTITIS

BACKGROUND OF THE INVENTION

The invention relates to a method of therapy for treating cows effected by subclinical or clinical mastitis and the subsequent nutritional maintenance of the cows to control, or minimize, reoccurrence of mastitis and to a composition useful therein.

Mastitis is the most underestimated single disease that effects dairy cattle. This profit stealer is so insidious and unspectacular that even dairymen working with it daily fail to understand its full importance.

Mastitis is the inflammation of the mammary gland regardless of the cause. The disease is characterized by the presence of a significantly increased leukocyte content in the milk from effected glands.

The definition of mastitis arrived at by the International Dairy Confederation requires the finding of pathogenic microorganisms in the milk and also a concentration of somatic cells in excess of 500,000/ml. This combination of criteria protects against misdiagnosis arising from contamination of the milk with bacteria from the external environment. This combination of criteria also permits one to distinguish between a pathogen population actually established in the gland and one that is merely harbored in the streak canal.

The simplest method for detecting mammary inflammation has been the indirect estimation of leukocytic infiltration of the gland by one or another of the so called screening tests. The California Mastitis Test (CMT) and the Kendall Mastitis Test (KMT) are methods of choice in the field.

The value of the screening tests may better be appreciated when one considers that the clinical syndrome may vary from a preacute inflammation, with toxemia, to a fibrosis which develops so gradually that it may escape observation until most of the secretory tissue has been destroyed. There is, of course, the additional danger that the bacterial contamination of milk from affected cows may render it unsuitable for human consumption or interfere with manufacturing processes and in rare cases even provide a mechanism which would spread disease to humans. Tuberculosis, streptococcal sore throat and brucellosis may be spread in this way.

In most countries, surveys of the incidence of mastitis, irrespective of cause, show comparable figures of about 40% morbidity amongst cows and a quarter incidence of about 25%. Most estimates show that on the average an affected quarter suffers a 30% reduction in productivity. An affected cow is estimated to lose 15%, or more, of its production.

While it is recognized that to prevent new intramammary infections, good sanitation continues to be of primary importance, to achieve good sanitation, several factors should be given special consideration. Factors such as nutrition, climate, and stress probably influence new infection rates, but there is insufficient evidence at this time to assess their influence.

Mastitis control should be based on preventing new infections in cows during lactation and eliminating infections in the nonlactation period. In devising a practical control program is necessary to concentrate on those factors which will substantially reduce the new infection rate.

In cases of chronic clinical mastitis, it must be taken into consideration that treatment is generally done by dairymen using over-the-counter products. This is not to say that veterinarians should not be consulted by dairymen with respect to overall management of their mastitis control program.

For economic reasons, the success of a control program is measured not only by the extent of the decrease in the level of infection but also by how quickly this is achieved. If a control program is to reduce levels of infection appreciably within a reasonable time, methods used must deal with all infections, not just those new infections in lactating cows, which may only comprise 50% of the total number of infections.

At the present time the principal means of decreasing the level of infection is through use of antibiotics. As a practical matter due to the fact that antibiotics are often times rather specific in their action, the dairymen must of necessity generally rely upon the services of a veterinarian, with associated appropriate laboratory facilities for identification of causative organisms.

As is well recognized by knowledgeable scientists a list of microorganisms associated with bovine mastitis is quite extensive both with regard to genus and species.

Mastitis research workers approximate that 90 to 95% of all cases of mastitis are caused by four species of bacterial cocci, i.e., *Staphylococcus aureus, Streptococcus agalactiae, Streptococcus dysgalactiae*, and *Streptococcus uberis*. The 90 to 95% figure refers, generally, to results of herd survey studies where organisms causing subclinical mastitis predominate.

The next most important group of pathogens are the bacilli, including *Escherichia coli, Enterobacter aerogenes, Klebsiella pneumoniae, Pseudomonas aeruginosa,* and *Corynebacterium pyogenes*. Occasional outbreaks have been reported for lesserknown organisms such as actinomycetes, fungi, yeasts, mycoplasma, rickettsia, viruses, and algae. Infections with these organisms tend to be of shorter duration than for the cocci, and the incidence of clinical disease is significantly higher.

Thus the wide variety of pathogens responsible for mastitis, and differences in epidemiologic patterns, compound the problem of preventing, treating and controlling the disease.

Individual cases of mastitis vary widely in severity and duration, but for purposes of convenience each case may be defined as clinical or subclinical.

Clinical mastitis is accompanied by obvious changes in the appearance of the milk and the affected quarter. Milk may include flakes or clots and the quarter may be hot, swollen, and sensitive.

Subclinical mastitis results in changes in the milk and secretory tissue of the udder that cannot be observed visually and can be detected only with a sensitive screening test or by culturing those samples in a laboratory to determine the presence of mastitis organisms. Subclinical mastitis is estimated to be present in about 50% of all dairy cows in an average of two quarters each. This form is 15 to 40 times more common than the clinical form and most clinical cases are preceded by subclinical cases.

As indicated, at the present time, the principal means for increasing the rate of elimination of infections is by using antibiotics to treat clinical and subclinical mastitis together with similar therapy of nonlactating cows in a control program that also includes good milking machine management and a hygiene routine that includes both premilking and postmilking teat disinfection.

In this latter regard numerous U.S. patents propose compositions for external application to the udder and teats of cows to aid in the prevention of mastitis. Representative of such patents are U.S. Pat. Nos. 3,728,449; 3,950,554; 3,993,777; and 4,012,504. It is believed that the compositions proposed in these patents are such that rely upon the known topical microbicidal action of iodine, and inorganic iodide or an indophor as the biologically active constituent of the composition.

However, there is an increasing awareness that measures such as teat dipping and therapy of nonlactating cows are not effective against coliform organisms, by far the most important environmental pathogens. Further, most microorganisms have demonstrated an uncanny ability to develop tolerance to antibiotics. It is axiomatic that the development of new antimicrobial agents should thus be encouraged.

Despite the accumulated knowledge about bovine mastitis, too few of the persons concerned with milk production are fully aware of the economic advantages of mastitis reduction techniques.

The economic advantage, or impact, of mastitis can better be appreciated when it is realized that of over an estimated two hundred million dairy cows world wide, 35 to 40% are estimated to be affected by mastitis. Losses in 1976 due to bovine mastitis, according to U.S.D.A., has been estimated to exceed one billion dollars in the U.S. alone, and this represents the effect of mastitis on only 5% of the world dairy population. While world figures are sketchy, projections from the U.S.D.A. figures reveal a world wide loss figure exceeding twenty billion dollars annually. Thus, if mastitis could be contained, i.e., at a level of less than about 5% infection on U.S. dairy farms, the net profit from dairying could be tripled.

For an in depth consideration of the economic problems of mastitis, reference is made to the paper entitled Mastitis Losses, authored by Charles N. Dobbins, Jr., DVM, Journal of the American Veterinary Medical Association, volume 170, no. 10, May 15, 1977, pages 1129-1132. In a direct quote from page 1129 of the paper the author states "The tragedy of mastitis losses is that the average diaryman usually does not recognize the 2 major losses (production loss and replacement cost). If you ask a dairyman what his mastitis losses are, he will generally refer to veterinary fees, drug costs, and discarded milk, since he pays for these out of his pocket. These losses, however, are relatively insignificant when compared with production loss and increased replacement cost."

Thus, the main object of the present invention is to reduce economic losses caused by intramammary infection.

It is another object of the present invention to provide a composition and method for the treatment and control of bovine mastitis.

It is a further object of the present invention to provide a non-antibiotic composition and method of utilizing the same which can be safely and economically utilized by dairymen to effectively treat and control bovine mastitis.

It is still another object of the present invention to provide such a composition that may be administered orally or parenterally.

SUMMARY OF THE INVENTION

These and other objects are accomplished according to the present invention which is based on the discovery that an extremely effective composition for the treatment and control of clinical and subclinical bovine mastitis comprises as effective constituents elemental iodine, potassium iodide and an aqueous solution of acetic acid made from the alcoholic and subsequent acetous fermentations of the juice of apples, which composition is administered in an aqueous carrier.

Since the amount of iodine and potassium iodide as opposed to the described aqueous solution of acetic acid are preferably selectively varied during utilization thereof in treatment of clinical and subclinical mastitis, as well as during utilization thereof for control of mastitis, the composition of the present invention is preferably prepared as two separate components.

As will become more apparent from a more detailed description of the invention the two components containing the active constituents of the composition are always utilized in conjunction with one another for systemic mastitis therapy and control.

With respect to the therapy aspect of the present invention, for mastitis to be eliminated from an infected quarter, one must get an effective antimicrobial agent to the site of infection at therapeutic levels for a sufficient duration of time, that is, until all affending organisms are killed or phagocytized.

One significant factor that must be taken into consideration in this regard are the physicochemical properties of the particular antimicrobial agent and the vehicle or carrier. Thus, while extensive work has been done in the field of systemic therapy and control of bovine mastitis there is still a need for better understanding of drug distribution to sites of infection in mastitic quarters, and it will be appreciated that as the description of the invention proceeds that it is theorized that latentiation plays a significant role in the delivery of the pharmacologically effective constituents of the composition to the mammary gland and wherein the effective constituents coact to provide a synergistic effect.

DETAILED DESCRIPTION

The composition of the present invention, to enable the administration of an efficacious dosage for the particular clinical situation encountered, is prepared in two component portions. For purposes of the following description and data with respect to pharmacodynamic results varified by clinical experience in the field, the component portions of the composition of the invention are set forth as effective constituents in aqueous solution.

However, it will be appreciated that description of the effective constituents in aqueous solution is by no means intended to limit the compounding of the composition of the present invention in a form other than as an aqueous solution thereof so long as the composition as administered is in a form that affects systemic delivery of the composition to the mammary gland in an efficacious amount.

In this regard, it will be appreciated that the effective constituents of the composition of the present invention may be provided in a concentrated form, which concentrate may even be provided as a substantially dry concentrate such as, for example, a utilization of well-known freeze drying techniques and wherein in a preferred mode of administration the concentrate is mixed with a systemically acceptable grade of water to provide the dosage form of the composition. Alternatively, it will also be appreciated that other well-known dosage forms may be utilized, such as, for example, but not limited to, encapsulated aqueous liquid or gelled forms thereof.

In the preferred mode of carrying forth the invention the first component of the composition is prepared by dissolving potassium iodide in water and then dissolving otherwise water insoluable elemental iodine in the aqueous potassium iodide solution.

A preferred formulation for the iodine-potassium iodide aqueous solution comprises;

50 g $I_2$
100 g KI
q.s. $H_2O$ to 1,000 ml

It will be appreciated of course that all constituents of the composition of the present invention, including the vehicle or carrier is of a suitable grade and preferrably USP grade.

In the preferred mode of carrying forth the present invention by provision of the composition as two components, the second component comprises an aqueous solution of acetic acid made from the alcoholic and subsequent acetous fermentations of the juice of apples. In this regard, for purposes of the present invention distinction is made between the aqueous solution of acetic acid derived as described and an aqueous solution of acetic acid derived from the pure compound or the alcoholic and subsequent acetous fermentations of alcohol derived from sources other than the juice of fruit and preferably the juice of apples.

As indicated previously, the efficacy of the method and composition of the present invention is theorized to be derived from the synergistic effect of the essential constituents comprising iodine, potassium iodide and an aqueous solution of acetic acid derived as described and the latentiation characteristics thereof for delivery to the site of the inflammation, namely the mammary gland.

Thus, it will be appreciated that an aqueous solution of acetic acid preferrably made from the alcoholic and subsequent acetous fermentations of the juice of apples includes in addition to the major proportion of acetic acid minor amounts of constituents of determined constitution and minor amounts of constituents of undetermined constitution.

In this regard, references made to the following table with respect to an analysis of an aqueous solution of acetic acid derived from the alcoholic and acetous fermentations of apple juice.

TABLE I

|  | Filtered | Cleared |
|---|---|---|
| Sp. gr. $\frac{15° C.}{15° C.}$ | 1.0193 | 1.0153 |
| Alcohol % by vol. | 0.04 | 0.055 |
| Glycerol | 0.235 | 0.245 |
| Solids | 1.315 | 1.205 |
| Sugars as invert |  |  |
| Before inversion | 0.45 | 0.45 |
| After inversion | 0.12 | 0.11 |
| Non-sugar solids | 1.19 | 1.10 |
| Volatile reducing substances | 0.33 | 0.34 |
| Total acid as acetic | 6.47 | 6.63 |
| Volatile acid as acetic | 6.44 | 6.58 |
| Fixed acid as malic | 0.03 | 0.055 |
| Volatile esters as ethyl acetate | 0.80 | 0.88 |
| Pentosans | 0.083 | 0.076 |
| Formic acid | 0.0004 | 0.0004 |
| Ash | 0.30 | 0.31 |
| Alkalinity of ash ml. 0.1 N acid per 100 ml. |  |  |
| Soluble ash | 34.5 | 34.6 |
| Insoluble ash | 5.8 | 5.9 |

The acetic acid concentration of the aqueous solution of acetic acid derived as described is preferably in the order of about 4 to 6 percent.

As will be appreciated by those of skill in the art of production of aqueous solutions of acetic acid by fermentation, the "acetic acid solution" varies in chemical composition on the basis of the substances from which it is fermented. While the preferred aqueous acetic acid solution utilized in the veterinary pharmaceutical composition of this invention is derived from the alcoholic and acetous fermentations of apple juice, other fruit juice derived aqueous acetic acid solutions may in fact be suitable, but their efficacy has not been verified by clinical tests. However, attempts to substitute an aqueous solution of acetic acid made by the acetous fermentation of dilute distilled alcohol has not in the course of clinical testing of cows affected with subclinical or clinical mastitis provided data that is at present considered to clearly establish the efficacy of such compositions utilizing the substituted acetic acid solution. This is not to say however that the present inability to verify the efficacy by clinical testing of a composition in accordance with the invention utilizing the substitute acetic acid solution might have been inconclusive for reasons other than the use of the substitute acetic acid solution. Thus, additional clinical testing in this regard may well be warranted.

As briefly touched upon previously, it will be appreciated that as is known in the art of the production of aqueous acetic acid solutions by fermentation procedures it is possible to concentrate such solutions without thermal degredation of the thermally liable organic trace constituents of such aqueous acetic acid solutions. Accordingly, utilization of aqueous acetic acid solutions derived from the alcoholic and acetous fermentations of fruit juice, and preferably apple juice, for example, by freeze drying and or vacuum concentration at low temperature are procedures within the scope of the invention for the production of the inventive composition in concentrated form.

While it is believed that the alcoholic and acetous fermentations of fruit juices, and preferably apple juice, for the production of an aqueous solution of acetic acid present in a concentration of about 4% to 6% is well known, specific reference is made herein to an exemplary fermentation process as disclosed in U.S. Pat. No. 2,419,286, the disclosure of which is hereby incorporated by reference.

In addition, it will be appreciated that the utilization of a "concentrate" of an appropriate aqueous solution of acetic acid also encompasses adsorption, or absorption, of the aqueous solution on a particulate carrier which more likely than not would merely comprise a substance that is inert with respect to the systemic pharmacological effect of the composition of the present invention. However, it will also be appreciated that in some instances it may be possible to tailor the concentrated form of a composition in accordance with the present invention to utilize a particulate solid that might for example add to the acceptability of an oral dosage form of the composition, or enhance the systemic tolerance of a parenteral dosage form of a composition in accordance with the present invention.

As previously discussed, and as will become even more apparent from consideration of clinical test data to be set forth and discussed, the method of therapy and control of mastitis in accordance with the present invention first entails utilizing a suitable recognized screening test, such as for example, the KMT, preferably on intermittent but continuing basis to not only verify the presence of clinical mastitis with respect to a particular cow but to also, and possibly even more importantly, ascertain the presence of subclinical mastitis. It will be appreciated that all lactating animals in a given herd should be continuously monitored in this manner and that nonlactating animals in the herd should be carefully monitored for any evidence whatsoever of the possibility of the onset of mastitis at the anticipated time of freshening. In this latter regard and as will be apparent from the following clinical test data the specific systemic pharmacological or pharmacokinetic mechanism is not presently known, but it has been clinically determined that treatment of a pregnant nonmastitic cows with the composition of the present invention appears to have utility with regard to minimizing complications attendant calving.

While not wishing to be bound to any theory, it is believed that the beneficial results provided by the present composition with respect to this aspect of dairying is most likely attributable to an improvement in the overall condition of the animal by utilization of the present composition. In this regard, it may very well be that the composition aids with respect to Krebs Cycle, i.e., the tricarboxylic acid cycle (TCA cycle), which is the special mechanism in the normal metabolism of living cells for the final degradation of 2-; 3-, or possibly 4-carbon metabolites by a combination of decarboxylation and dehydrogenation.

Since an efficacious dose of the composition in accordance with the present invention is of course interrelated with the body weight of an animal being treated for the therapy of a subclinical or clinical mastitic condition, or control, i.e., the maintenance of a nonmastitic condition, whether the animal is lactating or nonlactating, it will be appreciated that the dosages discussed are exemplary.

In the clinical test data to be discussed with respect to verification of the pharmacodynamic results obtained by clinical experience in the field the dairy herd comprised approximately 200 Holstein or Holstein-Friesian dairy cattle having an average body weight of about 1500 pounds to about 1600 pounds.

With respect to specific exemplary dosages with respect to the treatment of advanced cases of clinical mastitis, which it will be appreciated may even present the problem of avoiding morbidity, a cow so involved would as a general rule, for the initial 48 hours to 72 hours of treatment be administered relatively large dosages of the components comprising the composition of the present invention and the preferred route of administration during this initial period of treatment is by administration of the composition in aqueous solution as a drench, i.e., wherein the composition is administered with a syringe directly into the mouth of the animal to force the animal to drink the composition. Understandably, if the progression of the disease is such that the animal is actually down, and for one reason or another the composition cannot be administered in this manner the most probable parenteral route of administration would be IV.

With further reference to dosage of cattle of the above stated body weight an initial dosage by drenching would, for example, comprise the administration of an aqueous solution of:
  180.0 ml acetic acid solution
  180.0 ml water
  0.2 ml $I_2$-KI solution Thereafter, preferably at two hour intervals, such as subsequent to the initial dosing as above at morning milking, for example, the dosing of the cow would proceed as follows:

Approximately two hours after the above initial dosing the cow would again be drenched with a composition in the following ratio:
  180.0 ml acetic acid solution
  180.0 ml water
  7.5 ml $I_2$-KI solution It will be seen that the two initial doses respectively insure that the animal will tolerate the composition without adverse effect and then receive, what will be apparent hereinafter, a relatively massive dose of the $I_2$-KI component of the composition.

Optionally, if there appears to be a problem with the animal accepting the composition it has been found useful to include approximately 2 to 10 ml of molasses to the composition to enhance acceptability.

Subsequent to the above second relatively massive dose of the $I_2$-KI solution the cow would for example, be again drenched with the composition components in the following ratio;
  180.0 ml acetic acid solution
  180.0 ml water
  0.3 ml $I_2$-KI solution Two hours hence the animal would again then be drenched with the composition and preferably in the ratio set forth with regard to the initial drenching.

At subsequent intervals of two hours until the next milking the cow would again then be drenched alternately with a relatively large dosage of the $I_2$-KI solution, namely 7.5 ml thereof together with the amount of acetic acid solution and water utilized in the initial drenching, and dosages of 180.0 ml acetic acid solution plus 180.0 ml water and between about 0.3 and 0.4 ml $I_2$-KI solution.

The foregoing has generally been found to significantly reduce, if not even eliminate clinical mastitis in most animals under treatment and the foregoing dosages are then preferably augmented by administration, again such is by drenching, at both morning and evening milking of the composition in the following ratio;
  60.0 ml acetic acid solution
  30.0 ml water
  0.2 ml $I_2$-KI solution The latter dosage will be understood to comprise what is considered to be a maintenance dosage once the animals clinical or subclinical mastitic condition has been brought under control.

Thus, irrespective of whether the cow has freshened with a mastitic condition, is actively lactating, or is nonlactating, the latter described maintenance dosage has by clinical testing been found to be advisable. As a matter of fact, as a test control measure the maintenance dosage treatment was withdrawn subsequent to the test period graphically illustrated in the following tables and it was found that as a general rule within approximately three months substantially all of the mastitic cows that had been substantially alleviated of the condition, with attendent general increase in milk production, were generally all again mastitic with an attendent drop in production of milk.

In the following Tables comprising II, III, IV, and V the 48 cows subjected to clinical testing are from the aforedescribed herd comprising approximately 220 cows, about 200 of which were lactating.

Before entering into a specific discussion of the clinical test data of Tables II-V, it will be understood that the most practical mode of administering the described maintenance dosage is for all practical purposes to apply the composition in the component ratio described to the cows feed ration at morning and evening milking. In this regard, it has been found useful to optionally include the above described small amount of molasses to overcome any reluctance toward acceptability such as may be occasioned by the acetic acid solution - iodine solution aroma on the feed.

With respect to an interpretation of data recorded in the Tables with respect to the clinical test conducted it will be seen from the headings that the herd number and test number of the particular cow, age and clinical condition prior to treatment is recorded in the first four columns. Reference is made to Table V including a legend with respect to the clinical condition of each animal. In Tables II–IV it will be seen that the KMT was utilized on May 8, namely day one of the test, to determine the pretreatment clinical condition of animals numbers 1-30, 33, 34, and 36-41 and wherein test animals numbers 31, 32 and 35 did not undergo testing until two days hence.

TABLE II

| Number | | | Clinical Condition pretreatment | Test date May 8 | | | | Milk PH | Days Treat. | Last test date | | | | | Milk PH | Clinical Condition after treat. | Conclusions | | | Remarks |
|---|---|---|---|---|---|---|---|---|---|---|---|---|---|---|---|---|---|---|---|---|
| HERD NO. | TEST NO. | Age | | LF | LR | KMT RR | RF | | | LF | LR | KMT RR | RR | RF | | | Milk production 9th | 22nd | | |
| 420 | 1 | 9y8m | ++ | 2+ | 2+ | 2+ | 2+ | 7.5 7.5 7.5 7.5 | 7 | May 16 0 | 0 | 0 | 0 | | 6.0 6.0 6.0 6.0 | 0 | 23Lbs | 33Lbs | Group A | |
| 509 | 2 | 3y5m | ++ | Dry | 2+ | Dry | 2+ | 7.5 7.5 7.5 | 7 | May 16 0 | 0 | 0 | 0 | | 6.0 6.0 6.0 | 0 | 27 | 31 | | |
| 501 | 3 | 6y10m | ++(+) | 2+$_p$ | 2+$_p$ | 2+$_p$ | 2+$_p$ | 7.5 7.5 7.5 7.5 | 7 | May 16 0 | 0 | 0 | U | | 6.0 6.0 6.0 7.0 | θ | 0 | 43.5 | | Delivered healthy calf 5-11-77 |
| 545 | 4 | 5y8m | ++ | 2+ | 2+ | 2+ | 1.3 | 7.5 7.5 7.5 7.5 | 7 | May 16 0 | 0 | U | 0 | | 6.0 6.0 6.0 6.0 | 0 | 44 | 47 | Cases | |
| 652 | 5 | 2y8m | ++(+) | 2+ | 2+$_p$ | 2+ | 2+ | 7.5 7.5 7.5 7.5 | 9 | May 18 0 | 0 | 0 | 0 | | 6.0 6.0 6.0 6.0 | 0 | 0 | 35 | | |
| 637 | 6 | 3y2m | ++ | 2+$_p$ | 2+$_p$ | 2+$_p$ | 2+$_p$ | 7.5 7.5 7.5 7.5 | 7 | May 16 U | U | U | 0 | | 7.5 7.0 6.0 6.0 | θ | 39 | 43 | Severe | Delivered healthy calf 5-14-77 |
| 484 | 7 | 7y1m | ++(+) | Dry | 2+ | 2+ | 2+ | 7.5 7.5 7.5 | 7 | May 16 0 | 0 | U | U | | 6.0 7.5 7.5 | θ | 4 | 4 | | SOLD 5-21-77 |

P = Pus
U = Unknown organism still present (nonmastitic)
KMT = Kendall Mastitis Test
Clinical Condition
\+ = Poor
++ = Critical
++(+) = Chronic
0 = No Mastitis
θ = No Mastitis-Non mastitic unknown organism still present

Table III

| Number | | Clinical Condition pretreatment | Age | Last date May 8 KMT | | | | Milk PH | Days Treat. | Last test date KMT | | | | Milk PH | Clinical Condition after treat. | Conclusions Milk production | | Remarks |
|---|---|---|---|---|---|---|---|---|---|---|---|---|---|---|---|---|---|---|
| HERD NO. | TEST NO. | | | LF | LR | RR | RF | | | LF | LR | RR | RF | | | 9th | 22nd | |
| 458 | 8 | + (+) | 8y11m | Dry | 2 | 2 | 2 | 7.5 7.5 7.5 7.5 | 11 | May 20 U | 0 | 0 | 0 | 6.0 6.0 6.0 6.0 | θ | 34 | 36 | Cured Mastitis/Nonmastitic unknown organism still present |
| 457 | 9 | + (+) | 9y10m | 2 | 2 | 2 | Dry | 7.5 7.5 7.5 | 11 | May 20 0 | 0 | 0 | U | 6.0 6.0 6.0 | θ | 17 | 16.5 | Cured Mastitis/Nonmastitic unknown organism still present |
| 507 | 10 | + (+) | 6y6m | 2 | 2 | 2 | 2 | 7.5 7.5 7.5 7.5 | 10 | May 19 0 | 0 | 0 | 0 | 6.0 6.0 6.0 6.0 | 0 | 35 | 36 | |
| 596 | 11 | + (+) | 4y4m | 2 | 2 | 2 | 2 | 7.5 7.5 7.5 7.5 | 11 | May 20 0 | 0 | 0 | 0 | 6.0 6.0 6.0 6.0 | 0 | 6 | 8 | |
| 597 | 12 | + (+) | 4y3m | 2 | 2 | 2 | 2 | 7.5 7.5 7.5 7.5 | 9 | May 18 0 | 0 | 0 | 0 | 6.0 6.0 6.0 6.0 | 0 | 47 | 48 | |
| 429 | 13 | + (+) | 9y5m | 2 | 2 | 2 | 2 | 7.5 7.5 7.5 7.5 | 10 | May 19 0 | 0 | 0 | 0 | 6.0 6.0 6.0 6.0 | 0 | 22 | 26 | |
| 455 | 14 | + (+) | 9y8m | 2 | 2 | 2 | 2 | 7.5 7.5 7.5 7.5 | 10 | May 19 0 | 0 | 0 | 0 | 6.0 6.0 6.0 6.0 | 0 | 52 | 55 | |
| 476 | 15 | + (+) | 7y8m | 2 | 2 | 2 | 2 | 7.5 7.5 7.5 7.5 | 8 | May 17 0 | U | 0 | 0 | 6.0 6.0 7.5 6.0 | θ | 38 | 38 | Group B |
| 553 | 16 | + (+) | 5y4m | 2 | 2 | 2 | 2 | 7.5 7.5 7.5 7.5 | 11 | May 20 0 | 0 | 0 | 0 | 6.0 6.0 6.0 6.0 | 0 | 40 | 45 | |
| 492 | 17 | + (+) | 7y1m | 2 | 2 | 2 | 2 | 7.5 7.5 7.5 7.5 | 9 | May 18 0 | 0 | 0 | 0 | 6.0 6.0 6.0 6.0 | 0 | 8 | 10 | |
| 497 | 18 | + (+) | 6y11m | 2 | 2 | 2 | 2 | 7.5 7.5 7.5 7.5 | 11 | May 20 0 | 0 | 0 | 0 | 6.0 6.0 6.0 6.0 | 0 | 34 | 40 | |
| 472 | 19 | + (+) | 7y8m | 2 | 2 | 2 | 2 | 7.5 7.5 7.5 7.5 | 10 | May 19 0 | 0 | 0 | 0 | 6.0 6.0 6.0 6.8 | 0 | 3 | 5 | |
| 483 | 20 | + (+) | 7y5m | 2 | 2 | 2 | 2 | 7.5 7.5 7.5 7.5 | 11 | May 19 U | 0 | 0 | U | 6.0 70 6.0 6.0 | θ | Pregnant 0 | 0 | Cured Mastitis/Nonmastitic unknown organism still present |

P = Pus
U = Unknown organism still present (nonmastitic)
KMT = Kendall Mastitis Test
Clinical Condition
+ = Poor
+ + = Critical
+ + (+) = Chronic
0 = No Mastitis
θ = No Mastitis - Nonmastitic unknown organism still present

TABLE IV

| Number | | | Clinical | Test date May 8 | | | | | Days | Last test date | | | | | Clinical | Conclusions | | Remarks |
| HERD No. | TEST No. | Age | Condition pretreatment | LF | KMT LR | RR | RF | Milk PH | Treat | LF | KMT LR | RR | RF | Milk PH | Condition after treat. | Milk production 9th | 22nd | |
| --- | --- | --- | --- | --- | --- | --- | --- | --- | --- | --- | --- | --- | --- | --- | --- | --- | --- | --- |
| 639 | 21 | 3y1m | +(+) | 2 | 2 | 2 | 2 | 7.5 7.5 | 11 | May 20 | 0 | 0 | 0 | 6.0 6.0 | 0 | 45 | 44 | |
| 550 | 22 | 5y6m | +(+) | 2 | 2 | 2 | 2 | 7.5 7.5 | 9 | May 18 | 0 | 0 | 0 | 6.0 6.0 | 0 | 27 | 30 | |
| 556 | 23 | 5y5m | +(+) | 2 | 2 | 2 | 2 | 7.5 7.5 | 3 | May 13 | 0 | 0 | 0 | 6.0 6.0 | 0 | 26 | 28 | |
| 563 | 24 | 5y2m | +(+) | 2 | 2 | 2 | 2 | 7.5 7.5 | 11 | May 20 | 0 | 0 | 0 | 6.0 6.0 | 0 | 8 | 10 | |
| 622 | 25 | 3y8m | +(+) | 2 | 2 | 2 | 2 | 7.5 7.5 | 8 | May 17 | 0 | 0 | 0 | 6.0 6.0 | 0 | 25 | 30 | |
| 532 | 26 | 6y1m | +(+) | 2 | 2 | 2 | Dry | 7.5 7.5 | 11 | May 20 | 0 | 0 | U | 6.0 7.5 | 0 | 16 | 18 | Cured Mastitis/Nonmastitic unknown orgnism still present |
| 583 | 27 | 5y5m | +(+) | 2 | 2 | 2 | 2 | 7.5 7.5 | 11 | May 20 | 0 | 0 | 0 | 6.0 6.0 | 0 | 20 | 20 | |
| 566 | 28 | 5y1m | +(+) | 2 | 2 | 2 | 2 | 7.5 7.5 | 8 | May 17 | 0 | 0 | 0 | 6.0 7.5 | 0 | 45 | 48 | Cured Mastitis/Nonmastitic unknown orgnism still present |
| 504 | 29 | 6y9m | +(+) | 2 | 2 | 2 | 2 | 7.5 7.5 | 7 | May 16 | 0 | 0 | 0 | 6.0 6.0 | 0 | 43 | 44 | |
| 646 | 30 | 2y9m | +(+) | 2 May 10 | 2 Dry | 2 | 2 | 7.5 6.0 | 2 | May 12 | 0 | 0 | 0 | 6.0 6.0 | 0 | 42 | 48 | |
| 564 | 31 | 5y2m | ++ | May 0 | 10 | 2 | 0 | 6.0 7.5 | 8 | May 17 | 0 | U | 0 | 7.5 7.5 | 0 | 35 | 37 | Cured Mastitis/Nonmastitic unknown orgnism still present |
| 610 | 32 | 4y0m | + | 0 | 1 | 0.5 | 0 | 6.0 7.0 | 1 | May 11 | 0 | 0 | 0 | 6.0 6.8 | 0 | 28 | 28 | |
| 615 | 33 | 3y7m | +(+) | 2 | 2 | 2 | 2 | 7.5 7.5 | 1 | May 10 | 0 | 0 | 0 | 6.0 7.5 | 0 | 40 | 62 | |
| 357 | 34 | 2y7m | +(+) | 1.5 May 1.8 | 1.5 10 1.8 | 2 | 2 | 7.5 7.5 | 2 | May 10 | 0 | 0 | 0 | 6.0 7.5 | 0 | 42 | 42 | |
| 590 | 35 | 4y5m | +(+) | 1.8 | 1.8 | 1.8 | 1.8 | 7.5 7.5 | 8 | May 17 | 0 | 0 | 0 | 6.0 7.5 | 0 | 18 | 22 | |
| 453 | 36 | 8y7m | +(+) | 2 | 2 | 2 | Dry | 7.5 7.5 | 7 | May 16 | 0 | 0 | 0 | 6.0 6.0 | 0 | 42 | 57 | Cured Mastitis/Nonmastitic unknown orgnism still present |
| 538 | 37 | 3y1m | 0 | | | | | | 5 | May 16 | 0 | 0 | 0 | 6.0 6.0 | 0 | 47 | 48 | Delivered calf 5-17-77 |
| 655 | 38 | 2y7m | 0 | Treatment given to (nonmastitic) pregnant cows to ease delivery | | | | | 5 | May 16 | 0 | 0 | 0 | 6.0 6.0 | 0 | 0 Pregnant 0 | 25 0 | Complications w/placenta-double treatment given placenta dislodged 24 minutes later |
| 387 | 39 | 10y11m | 0 | | | | | | 5 | May 16 | 0 | 0 | 0 | 6.0 6.0 | 0 | Pregnant 0 | 0 | |
| 436 | 40 | 9y4m | 0 | | | | | | 5 | May 16 | 0 | 0 | 0 | 6.0 6.0 | 0 | Pregnant 0 | 0 | |
| 616 | 41 | 4y9m | 0 | | | | | | 5 | May 16 | 0 | 0 | 0 | 6.0 6.0 | O | 0 | 0 | |

GROUP B

TABLE V

| Number | | | Clinical Condition pretreatment | Test date May 18 KMT | | | | Milk PH | Days Treat. | Test date May 20 KMT | | | | Milk PH | Clinical Condition after treat. | Conclusions Milk production | | Remarks |
|---|---|---|---|---|---|---|---|---|---|---|---|---|---|---|---|---|---|---|
| HERD NO. | TEST No. | Age | | LF | LR | RR | RF | | | LF | LR | RR | RF | | | 18th | 22nd | |
| 433 | 42 | 9y7m | ++(+) | 2+ | 2+ | 2+ | 2 | 7.5 7.5 | 2 | 0 | 0 | 0 | 0 | 6.0 6.0 | 0 | 20 lbs | 21 lbs | positive results were obtained in 48 hours |
| 473 | 43 | 7y8m | +(+) | 2 | 1.5 | 2 | 2 | 7.5 7.5 | 2 | 0 | 0 | 0 | 0 | 6.0 6.0 | 0 | 30 | 32 | Group |
| 528 | 44 | 6y2m | ++ | 1.5 | 2 | 2 | 2 | 7.5 7.5 | 2 | 0 | 0 | 0 | 0 | 6.0 6.0 | 0 | 6 | 8 | |
| 576 | 45 | 5y9m | (+) | 0 | 0 | 0.2 | 0 | 6.5 6.5 | 2 | 0 | 0 | 0 | 0 | 6.0 6.0 | 0 | 30 | 34 | Control Group |
| 427 | 46 | 10y6m | ++ | 2 | 2 | 2 | 1 | 6.5 7.0 | 2 | 0 | 0 | 0 | 0 | 6.0 6.0 | 0 | 18 | 17.5 | |
| 469 | 47 | 7y9m | ++ | 1.5 | 2 | 2+ | 1.5 | 7.5 7.5 | 2 | 0 | 0 | 0 | 0 | 6.0 6.0 | 0 | 36 | 35.5 | |
| 499 | 48 | 6y10m | ++(+) | 2 | 2 | 2+ | 2 | 7.5 7.5 | 2 | 0 | 0 | 0 | 0 | 6.0 6.0 | 0 | 41 | 38 | |
| | | | | | | | | | | | | | | | | 1503 | 1727 | 224 lbs increase in milk production 48 total cows during testing period |

P = PUS
U = Unknown organism still present (nonmastitic)
KMT = Kendall Mastitis Test
Clinical condition
+ = Poor
++ = Critical
++(+) = Chronic
0 = No Mastitis
θ = No Mastitis - Nonmastitic unknown orgnism still present From the test data with respect to test animals 1-7 it will be seen that these animals comprise animals characterized by a very severe, if not chronic, critical mastitic condition, even characterized by the discharge of pus from the teat canal. Treatment of cows 1-7 was carried forth as described above with a treatment dosages as set forth above for 72 hours after which the cows were placed on a maintenance dosage as described above and administration of the composition withdrawn in 7 to 9 days as set forth and wherein in addition to screening tests being continuously taken the last day of inclusion of the animal in the clinical test is set forth with regard to the condition of each quarter as per KMT with the recordation of the clinical condition after treatment and the milk production as with respect to the ninth day and twenty-second day of May, namely the second day of the test and the fourteenth day of the test.

Consideration of data of Table II is considered to be persuasive of the efficacy of the utilization of the composition of the present invention.

The test data recorded in Tables III and IV, which in fact comprise a second group of animals of test numbers 8-41, having less severe mastitic involvement were drenched as described above for between 48 and 72 hours and wherein the number of days of treatment indicated with respect to each animal exceeded the initial 48 to 72 hour drenching, the animals were placed on the maintenance dosage described above.

An interpretation of the KMT results on the last test date for each animal clearly supports the efficacy of the composition with respect to a statistically significant cross section of the animals so tested.

It will be noted that test animals 37-41 fall into a category of nonmastitic cows that underwent treatment for five days in an attempt to evaluate the utility of the composition of the present invention in improving the overall health of the animals, and with respect to test animal number 38 the cow calfed nine days after onset of treatment which, was discontinued five days subsequent to the onset of treatment and wherein complications that developed during calving due to failure of the placenta to separate and the cow was immediately placed on massive dosages which effected dislodgment of the placenta within a remarkably short period of time.

With further specific reference to Table V test animals numbers 42-48 were subjected to the same milking regimen, with the same equipment, as test animals 1-41, except of course with respect to clearly nonlactating cows 37-41 so as to provide a control group that did not undergo treatment until ten days after the onset of the test and wherein animals of test numbers 42-48 were drenched as indicated above for only 48 hours and then placed on a maintenance dosage with treatment extending for only two days. At the end of which period KMT results indicated an absence of clinical or subclinical mastitis.

In assessing the conclusions with respect to milk production, the production of each cow was charted, even with respect to the nonlactating cows. However, the data set forth in the Tables is considered sufficient to verify the efficacy of the composition of the present invention, particularly when one takes into consideration that even where milk reduction was not significantly increased as between the first and second recorded production figures the milk did not represent a production loss since it was in fact suitable for pasteurization and human consumption.

In addition, apparently by virtue of metabolic utilization of the essential constituents of the composition of the present invention it appears that substantially no untoward carry over of the effective constituents into the milk was experienced.

I claim:

1. A method for the treatment of mastitis in bovine udders which comprises systemically administering an effective amount of a composition comprising as essential constituents, iodine, potassium iodide, a dilute acetic acid derived from the juice of fruit and a carrier.

2. The method of claim 1 wherein the iodine and potassium iodide comprise an aqueous solution thereof.

3. The method of claim 1 wherein the dilute acetic acid is an aqueous solution thereof derived from the alcoholic and subsequent acetous fermentations of the juice of fruit.

4. The method of claim 3 wherein the dilute aqueous solution of acetic acid is derived from apple juice.

5. A composition for the systemic treatment of mastitis in bovine udders which comprises as essential constituents effective amounts of; iodine, potassium iodide, and a dilute acetic acid derived from the juice of fruit.

6. The composition of claim 5 wherein the iodine and potassium iodide comprise an aqueous solution thereof.

7. The composition of claim 5 wherein the dilute acetic acid is an aqueous solution thereof derived from the alcoholic and subsequent acetous fermentations of the juice of fruit.

8. The composition of claim 7 wherein the dilute aqueous solution of acetic acid is derived from apple juice.

* * * * *